United States Patent
Guo et al.

(10) Patent No.: US 12,305,098 B2
(45) Date of Patent: May 20, 2025

(54) LUMINESCENT PROBE AND ITS PREPARATION METHOD AND APPLICATION

(71) Applicant: East China University of Science and Technology, Shanghai (CN)

(72) Inventors: Zhiqian Guo, Shanghai (CN); Juan Li, Shanghai (CN); Yutao Zhang, Shanghai (CN); Yao Lu, Shanghai (CN); Chenxu Yan, Shanghai (CN); Meiling Zhao, Shanghai (CN); Xiuyan Zhao, Shanghai (CN); Weihong Zhu, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 18/768,028

(22) Filed: Jul. 10, 2024

(65) Prior Publication Data
US 2025/0066662 A1     Feb. 27, 2025

(30) Foreign Application Priority Data
Aug. 24, 2023 (CN) .................. 202311076428.X

(51) Int. Cl.
    *C09K 11/06*      (2006.01)
    *C07D 309/34*      (2006.01)
    (Continued)

(52) U.S. Cl.
     CPC ............ *C09K 11/06* (2013.01); *C07D 309/34* (2013.01); *C07D 407/10* (2013.01);
    (Continued)

(58) Field of Classification Search
None
See application file for complete search history.

(56) References Cited

FOREIGN PATENT DOCUMENTS

| CN | 111187247 A | 5/2020 |
|---|---|---|
| CN | 112469705 A | 3/2021 |

(Continued)

OTHER PUBLICATIONS

Kevin J. Bruemmer, et al., Chemiluminescent Probes for Activity-Based Sensing of Formaldehyde Released from Folate Degradation in Living Mice, Angewandte Chemie International Edition, 2018.

(Continued)

*Primary Examiner* — Xiaoyun R Xu
(74) *Attorney, Agent, or Firm* — Bayramoglu Law Offices LLC

(57) ABSTRACT

A luminescent probe and its preparation method and application are provided. The luminescent probe has a steric hindrance group $R_1$ of aliphatic hydrocarbon structure such as adamantane or norborneol, a detection group $R_2$ of nitrobenzyl and its derivative structure, an electron-withdrawing group $R_3$ containing cyano group and an electron-donating group methoxy group. In the presence of HSA or BSA, the detection group is cut off to form a parent structure that exposes atomic oxygen anions and is activated under external light irradiation, the luminescent probe can be used in solution or cells, when detecting HSA or BSA, the luminescent probe has obvious chemiluminescence characteristics, which can sensitively distinguish HSA and BSA, quantitatively analyze HSA and BSA, and determine the mixing ratio of HSA and BSA at the same time, and the luminescent probe has been successfully used for cell fluorescence imaging.

14 Claims, 9 Drawing Sheets

(51) Int. Cl.
*C07D 407/10* (2006.01)
*G01N 21/64* (2006.01)

(52) U.S. Cl.
CPC .. *G01N 21/6428* (2013.01); *C09K 2211/1088* (2013.01); *G01N 2333/765* (2013.01)

(56) References Cited

FOREIGN PATENT DOCUMENTS

| CN | 115417863 A | 12/2022 |
| CN | 116606220 A | 8/2023 |

OTHER PUBLICATIONS

Anna Bujacz, Structures of bovine, equine and leporine serum albumin, Acta Crystallographica, 2012, pp. 1278-1289, D68.

Alexander A. Ksenofontov, et al., Water-Soluble BODIPY-Based fluorescent probe for BSA and HSA detection, Journal of Molecular Liquids, 2022, pp. 1-9, vol. 345, 117031.

LUMINESCENT PROBE AND ITS PREPARATION METHOD AND APPLICATION

CROSS-REFERENCE TO THE RELATED APPLICATIONS

This application is based upon and claims priority to Chinese Patent Application No. 202311076428.X, filed on Aug. 24, 2023, the entire contents of which are incorporated herein by reference.

TECHNICAL FIELD

The present disclosure relates to the technical field of luminescence detection, in particular to a luminescent probe and its preparation method and application.

BACKGROUND

HSA is an important diagnostic biomarker in clinical practice. Abnormal HSA levels suggest serious health problems, such as liver failure, cirrhosis, chronic hepatitis, cardiovascular disease and cancer. Therefore, the accurate detection of HSA is of great significance in clinical diagnosis. HSA has been used as a biocompatible carrier in many research fields due to the presence of various hydrophobic cavities that accommodate hydrophobic molecules, for example, drug discovery and delivery, biomaterials and artificial plasma. However, it is worth noting that HSA is different from BSA. Because BSA has a similar structure and hydrophobic cavity to HSA, and BSA is cheaper than HSA, it is widely used to replace HSA in many biochemical and pharmacological applications. In fact, BSA has only 75.8% of the biological function of HSA (Biological crystallography, 2012, 68, 1278-1289), and cannot replace HSA for clinical treatment. Abusing two types of proteins may cause fatal harm to patients. Therefore, it is very important to develop an appropriate detection method to distinguish HSA and BSA. However, the detection sensitivity of the probes provided by the prior art (Journal of Molecular Liquids, 2022, 345, 117031) is not high enough, which limits its further application. Therefore, it is urgent to provide a highly sensitive luminescent probe and its preparation method for quantitative analysis of HSA and BSA.

SUMMARY

The purpose of the present disclosure is to provide a luminescent probe and its preparation method and application, to solve the problem that the detection sensitivity of HSA and BSA is not high in the prior art.

In order to achieve the above invention purpose, the present disclosure adopts the following technical solutions.

The present disclosure provides a luminescent probe, and the luminescent probe has a structural formula shown in Formula (I):

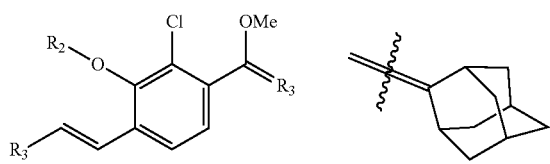

(I)

wherein, $R_1$ is selected from one of,

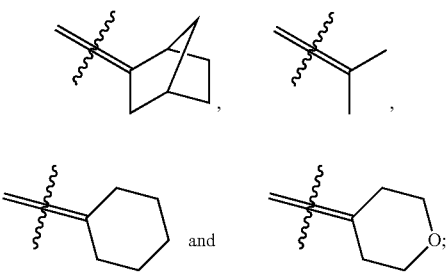

$R_2$ is selected from one of

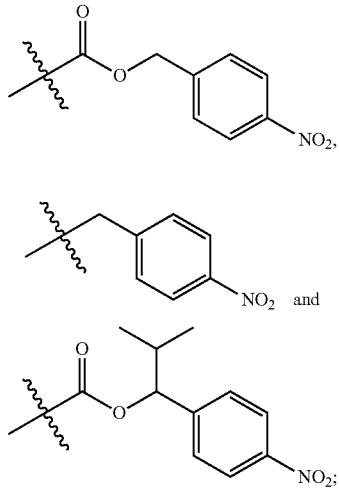

and $R_3$ is selected from one of

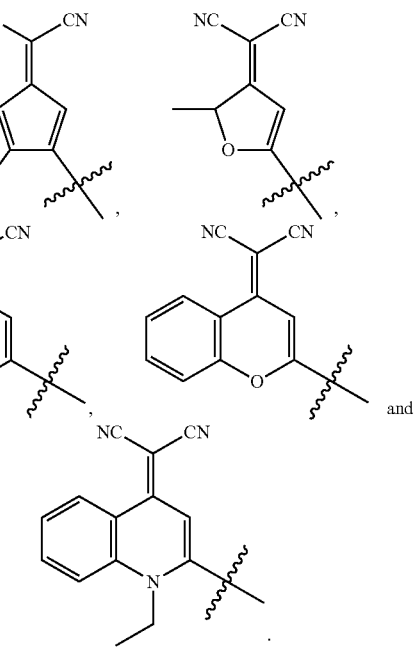

Preferably, a structural formula of the luminescent probe is

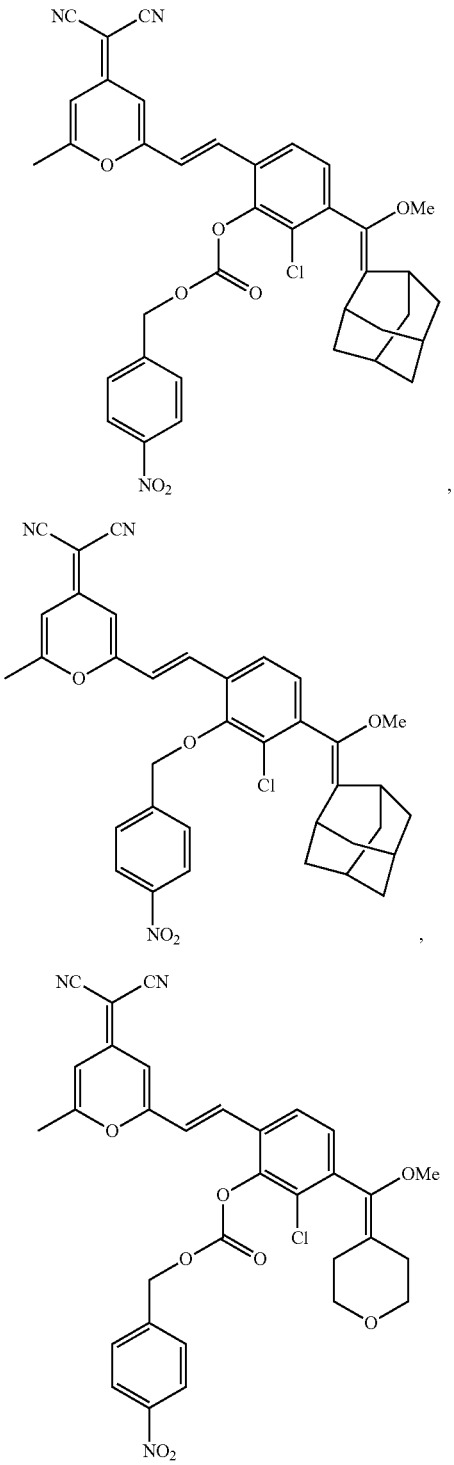

The present disclosure provides a preparation method for the luminescent probe, including the following steps:
(1) mixing 4-(dicyanomethylene)-2,6-dimethyl-4H-pyran, compound 1, acetonitrile and piperidine, then performing a reaction, to obtain a phenolic hydroxyl precursor;
(2) mixing the phenolic hydroxyl precursor, compound 2 and solvent, then cooling to 0° C., adding nitro compounds and performing a reaction, to obtain a luminescent probe with a structural formula (II), (III) or (IV); wherein in step(1), compound 1 is

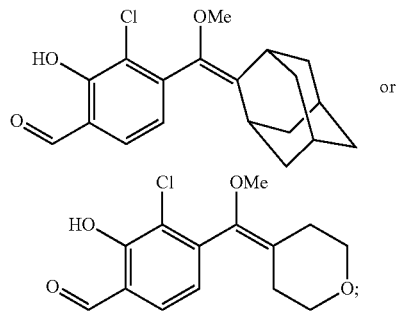

and
in step(2), compound 2 is triethylamine or cesium carbonate; the nitro compounds are benzyl 4-nitrochloroformate or 4-nitrobenzyl bromide.

Preferably, in step(1), a molar volume ratio of 4-(dicyanomethylene)-2,6-dimethyl-4H-pyran, compound 1, acetonitrile and piperidine is 0.6~2.5 mmol:0.6~2.5 mmol:20~30 mL:0.1~1 mL.

Preferably, in step(1), a reaction temperature is 20~30° C., and a reaction time is 5~7 h.

Preferably, in step(2), a molar volume ratio of the phenolic hydroxyl precursor, compound 2, the solvent, and the nitro compounds is 0.06-0.12 mol:0.1~0.2 mmol:15-25 mL:0.1~0.2 mmol.

Preferably, in step(2), a reaction temperature is 0~30° C., and a reaction time is 20~26 h.

The present disclosure provides an application of the luminescent probe in the detection of human serum albumin and bovine serum albumin, including the following steps: mixing a luminescent probe stock solution with mixed solvent and serum albumin stock solution in turn, afterwards, performing an incubation and detection in turn.

Preferably, a concentration of the luminescent probe stock solution is $0.8 \times 10^{-3}$~$1.5 \times 10^{-3}$ M; the mixed solvent is prepared from dimethyl sulfoxide and phosphate buffered saline (PBS) buffer solution, wherein a volume ratio of dimethyl sulfoxide and PBS buffer solution is 1:2~3, a pH value of PBS buffer solution is 7.0~7.5; and a concentration of the serum albumin stock solution is $2.0 \times 10^{-4}$~$1.0 \times 10^{-2}$ M.

Preferably, a volume ratio of the luminescent probe stock solution, the mixed solvent and the serum albumin stock solution is 20 μL:1.84~2 mL:0~160 μL; and an incubation temperature is 36.5~37.5° C., an incubation time is 42~46 min.

The beneficial effects of the present disclosure are:
(1) In the presence of HSA or BSA, the detection group of the luminescent probe provided by the present disclosure is cut off, to form a parent structure that exposes atomic oxygen anions, the parent structure requires external light source irradiation to activate, usually, a light intensity of 21 mW·cm$^{-2}$ requires illumination for 2~20 s, and the excitation light must include some or all bands of 400~600 nm.
(2) The luminescent probe of the present disclosure is a dual-mode high-sensitivity probe integrating chemiluminescence and fluorescence. After testing, the concentration of BSA and HSA shows a good linear relationship with the fluorescence signal and chemiluminescence signal of the probe. It is worth noting that in the same test system, the normalized fluorescence signal and chemiluminescence signal ratio of the probe after incubation with HSA and BSA at the same concentration are significantly different, and the former is about 6.2 times that of the latter. Moreover, with the increase of [HSA]/[HSA+BSA], the fluorescence signal and chemiluminescence signal of the probe also have an excellent quadratic function relationship. In summary, the probe can be used to sensitively distinguish HSA and BSA, quantitatively analyze HSA and BSA, and determine the mixing ratio of HSA and BSA at the same time, and it has been successfully used for cell fluorescence imaging. Meanwhile, the probe can be used as a cell imaging radiography agent.

(3) The fluorescence detection limit of the luminescent probe prepared by the present disclosure for HSA is as low as 10.25 nM, the chemiluminescence detection limit is as low as 8.21 nM, the fluorescence detection limit for BSA is as low as 17.41 nM, and the chemiluminescence detection limit is as low as 5.02 nM. Meanwhile, the probe has a dual-mode detection, which greatly improves the detection sensitivity.

(4) The luminescent probe prepared by the invention can be applied in aqueous solution and cells and has obvious chemiluminescence characteristics in vitro tests.

BRIEF DESCRIPTION OF THE DRAWINGS

FIGS. 1A and 1B show an ultraviolet absorption diagram and a fluorescence spectrogram of the luminescent probe 1 (10 μM) in Application Example 1 in DMSO/PBS (v/v=3:7) mixed solvent before and after response to HSA (100 μM), wherein FIG. 1A is the ultraviolet absorption diagram, and FIG. 1B is the fluorescence spectrogram;

FIGS. 2A-2C show a fluorescence spectrogram, a chemiluminescence intensity diagram and a normalized ratio comparison chart of fluorescence intensity and chemiluminescence intensity of probe 1 (10 μM) in Application Example 2 in DMSO/PBS (v/v=3:7) mixed solvent before and after response to HSA (20 μM) and BSA (20 μM), respectively, wherein FIG. 2A is the fluorescence spectrogram, FIG. 2B is the chemiluminescence intensity diagram, and FIG. 2C is the normalized ratio comparison chart of fluorescence intensity and chemiluminescence intensity;

FIGS. 3A and 3B show a linear relationship of the fluorescence signal and a linear relationship of the chemiluminescence signal at 615 nm after response of luminescent probe 1 (10 μM) provided in Application Example 3 in the mixed solvent of DMSO and PBS with different volume ratios to different concentrations of HSA (0~3.5 μM) or BSA (0~3.5 μM), respectively, wherein FIG. 3A is the linear relationship of the fluorescence signal, and FIG. 3B is the linear relationship of the chemiluminescence signal;

FIGS. 4A-4C show a linear relationship of the fluorescence signal and a linear relationship of the chemiluminescence signal at 615 nm after tresponse of luminescent probe 1 (10 μM) in Application Example 5 in DMSO/PBS (v/v=1:2) mixed solvent to different proportions of HSA and BSA mixed solution([HSA]+[BSA]=20 μM), wherein FIG. 4A is the linear relationship of the fluorescence signal, FIG. 4B is the linear relationship of the chemiluminescence signal, and FIG. 4C is a quadratic function diagram with protein ratio as abscissa and the normalized ratio of fluorescence signal to chemiluminescence signal as ordinate;

FIGS. 5A and 5B show a linear relationship of the fluorescence signal and a linear relationship of the chemiluminescence signal at 615 nm after response of luminescent probe 1 (10 μM) prepared in Embodiment 1 in DMSO/Tris-HCl/urine (v/v=6:7:7) mixed solvent to different concentrations of HSA (0~10 μM), wherein FIG. 5A is the linear relationship of the fluorescence signal, and FIG. 5B is the linear relationship of the chemiluminescence signal;

DETAILED DESCRIPTION OF THE EMBODIMENTS

Figure 1B:
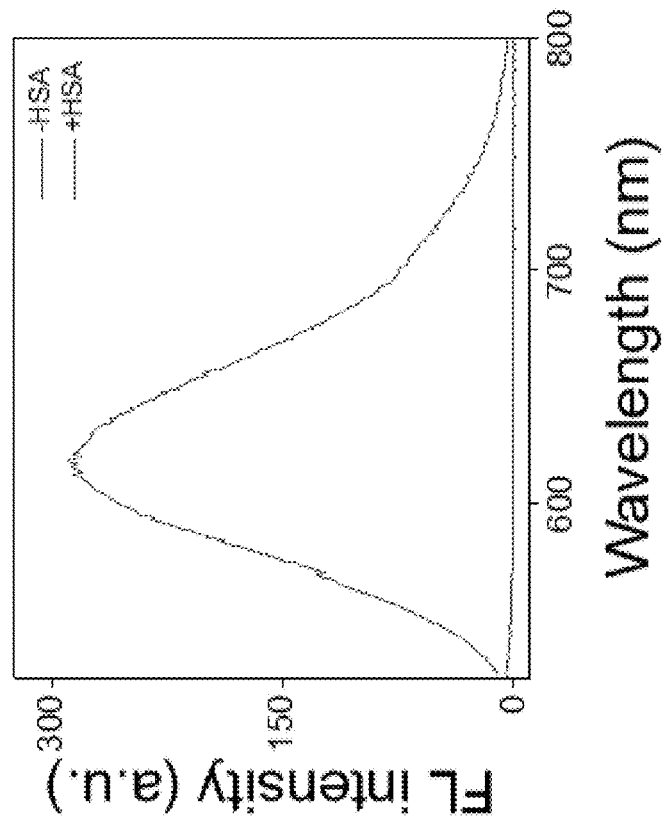

The present disclosure provides a luminescent probe, and the luminescent probe has a structural formula shown in Formula (I):

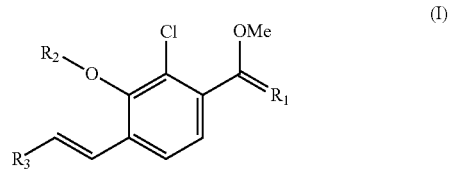

wherein, $R_1$ is selected from one of

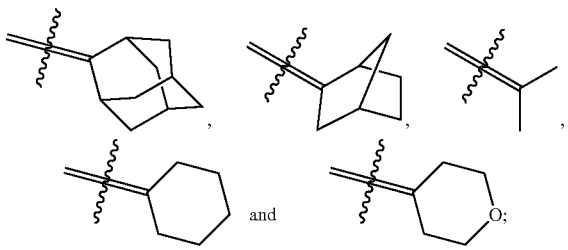

$R_2$ is selected from one of

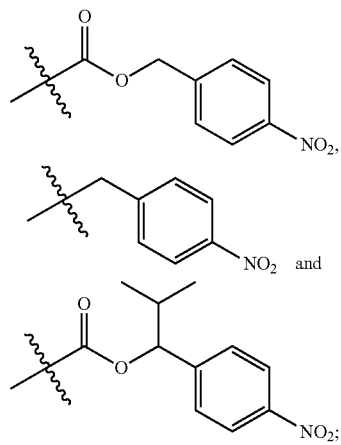

and R₃ is selected from one of
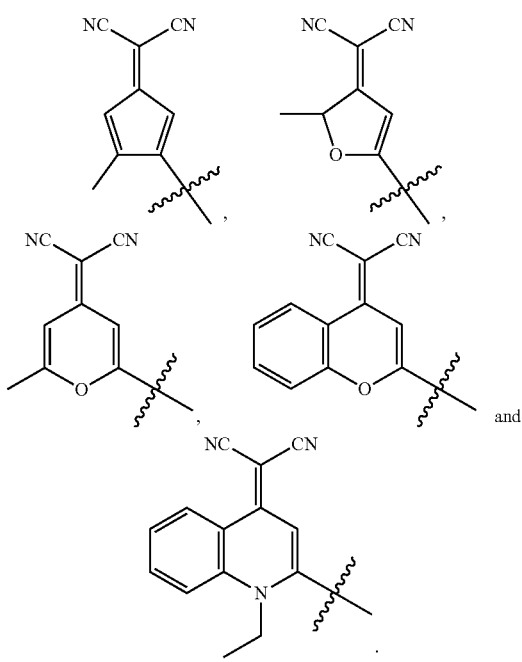,
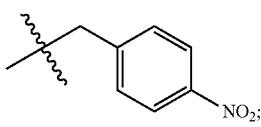
and R₃ is preferably one of
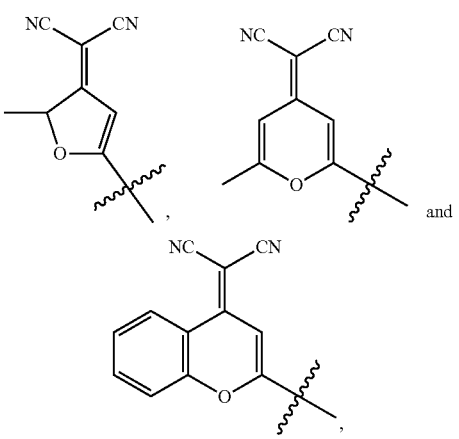
In the present disclosure, R₁ is preferably one of
further preferably
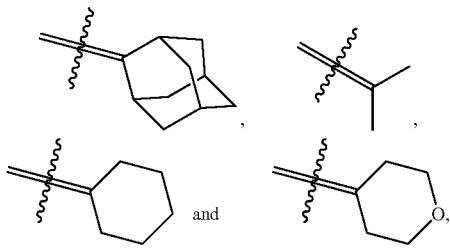
further preferably one of
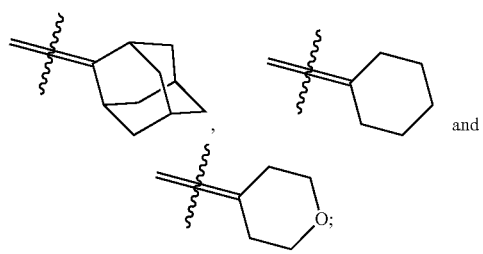
R₂ is preferably one of
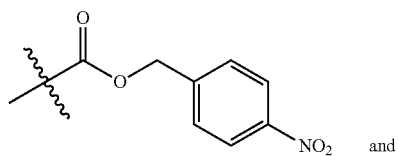
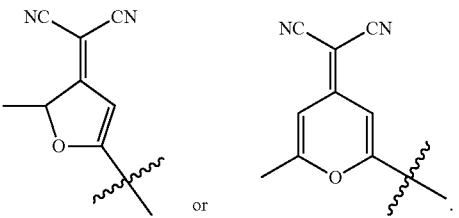 [SMILES: *C1=CC(=C(C#N)C#N)C(C)O1 ; *C1=CC(=C(C#N)C#N)C=C(C)O1]
In the present disclosure, a structural formula of the luminescent probe is preferably
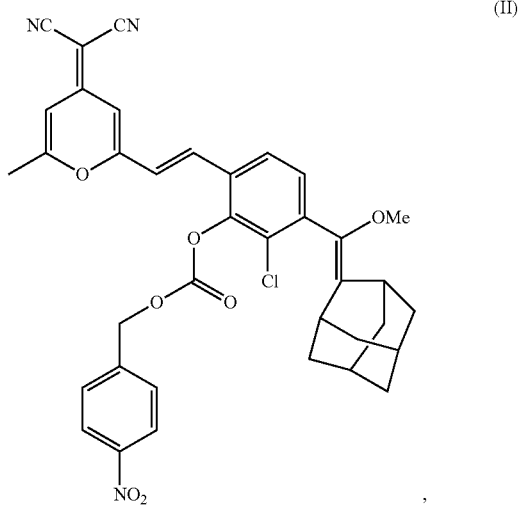
(II)

-continued

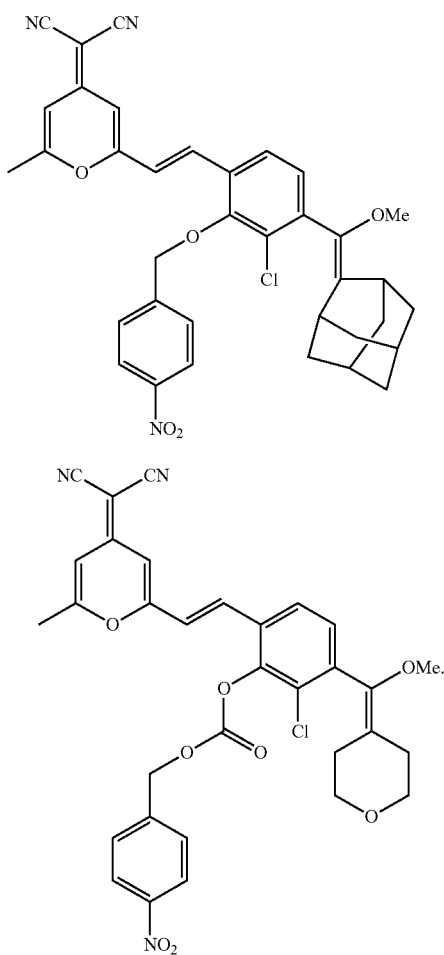

(III)

or (IV)

The present disclosure provides a preparation method for the luminescent probe, including the following steps:
(1) mixing 4-(dicyanomethylene)-2,6-dimethyl-4H-pyran, compound 1, acetonitrile and piperidine, then performing a reaction, to obtain a phenolic hydroxyl precursor;
(2) mixing the phenolic hydroxyl precursor, compound 2 and solvent, then cooling to 0° C., adding nitro compounds and performing a reaction, to obtain a luminescent probe with a structural formula (II), (III) or (IV); in step(1), compound 1 is

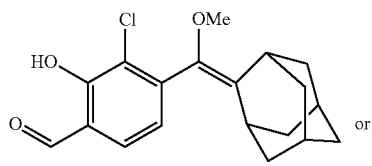

and in step(2), compound 2 is triethylamine or cesium carbonate; the nitro compounds are benzyl 4-nitrochloroformate or 4-nitrobenzyl bromide.

In the present disclosure, in step(1), a molar volume ratio of 4-(dicyanomethylene)-2,6-dimethyl-4H-pyran, compound 1, acetonitrile and piperidine is 0.6~2.5 mmol: 0.6~2.5 mmol:20~30 mL:0.1~1 mL, preferably 0.62~2.48 mmol:0.63~2.48 mmol:22~28 mL:0.3~0.8 mL, further preferably 0.67~2.45 mmol:0.65~2.45 mmol:24~26 mL:0.4~0.6 mL.

In the present disclosure, in step(1), a reaction temperature is 20~30° C. preferably 22~28° C., further preferably 25°° C.; and a reaction time is 5~7 h, preferably 5.5~6.5 h, further preferably 6 h.

In the present disclosure, in step(2), a molar volume ratio of the phenolic hydroxyl precursor, compound 2, the solvent, and the nitro compounds is 0.06-0.12 mol:0.1~0.2 mmol:15-25 mL:0.1~0.2 mmol, preferably 0.062~0.10 mmol:0.13~0.19 mmol:18~22mL:0.12~0.18 mmol.

In the present disclosure, in step(2), a reaction temperature is 0~30° C., preferably 0~25° C., further preferably 0° C. or 25° C.; and a reaction time is 20~26 h, preferably 21~25 h, further preferably 22~24 h.

The present disclosure provides an application of the luminescent probe in the detection of human serum albumin and bovine serum albumin, including the following steps: mixing a luminescent probe stock solution with mixed solvent and serum albumin stock solution in turn, afterwards, performing an incubation and detection in turn.

In the present disclosure, a concentration of the luminescent probe stock solution is $0.8 \times 10^{-3} \sim 1.5 \times 10^{-3}$ M, preferably $0.9 \times 10^{-3} \sim 1.3 \times 10^{-3}$ M, further preferably $1.0 \times 10^{-3} \sim 1.2 \times 10^{-3}$ M; the mixed solvent is prepared from dimethyl sulfoxide and PBS buffer solution, wherein a volume ratio of dimethyl sulfoxide and PBS buffer solution is 1:2~3, preferably 1:2.1~2.6, further preferably 1:2.2~2.4; a pH value of PBS buffer solution is 7.0~7.5, preferably 7.1~7.4, further preferably 7.4; and a concentration of the serum albumin stock solution is $2.0 \times 10^{-4} \sim 1.0 \times 10^{-2}$ M, preferably $8.0 \times 10^{-4} \sim 8.0 \times 10^{-3}$ M, further preferably $1.0 \times 10^{-3} \sim 5.0 \times 10^{-3}$ M.

In the present disclosure, a volume ratio of the luminescent probe stock solution, the mixed solvent and the serum albumin stock solution is 20 μL:1.84~2 mL:0~160 μL, preferably 20 μL:1.86~1.98 mL:20~140 μL, further preferably 20 μL:1.88~1.96 mL:40~120 μL; an incubation temperature is 36.5~37.5° C., preferably 36.7~37.2° C., further preferably 37° C.; and an incubation time is 42~46 min, preferably 43~45 min, further preferably 44 min.

In the presence of HSA or BSA, the detection group of the luminescent probe provided by the present disclosure is cut off, to form a parent structure of the exposed atomic oxygen anions, the parent structure requires external light source irradiation to activate, usually, the light intensity at 21 mW·cm$^{-2}$ requires illumination for 2~20 s, and the excitation light must include some or all bands of 400~600 nm, the specific detection principle is as follows:

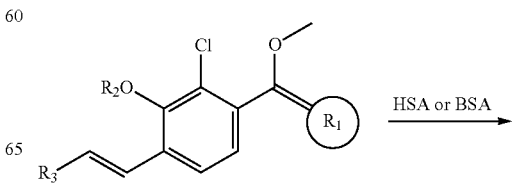

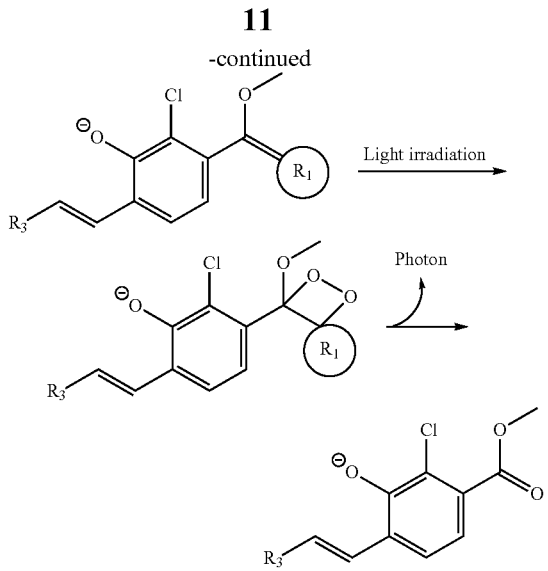

In the following, the technical schemes provided by the present disclosure are described in detail in combination with embodiments, but they can not be understood as limiting the scope of protection of the present disclosure.

Embodiment 1

0.70 mmol 4-(dicyanomethylene)-2,6-dimethyl-4H-pyran, 0.67 mmol compound 1, 25 mL acetonitrile and 0.5 mL piperidine were added to a 100 mL dry bottle with two necks, after mixing evenly, the reaction was performed at 25° C. for 6 h, after cooling, the organic solvent was removed by vacuum concentration, the crude solid obtained was purified by silica gel column chromatography, a yellowish-brown solid (61 mg, yield 11%) was obtained, that was a phenolic hydroxyl precursor, wherein compound 1 was

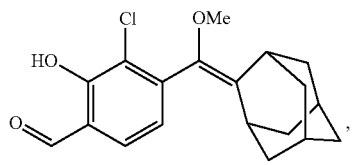 [SMILES: COC(=C1C2CC3CC(C2)CC1C3)c1ccc(C=O)c(O)c1Cl]

a structural formula of the phenolic hydroxyl precursor obtained was

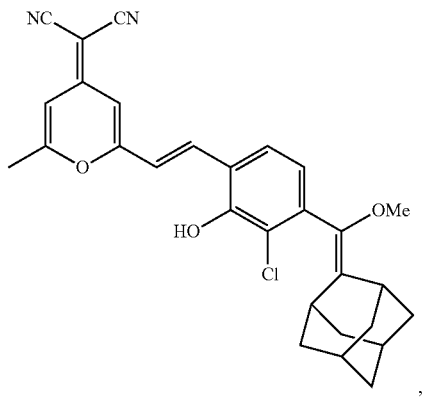 [SMILES: COC(=C1C2CC3CC(C2)CC1C3)c1ccc(/C=C/C2=CC(=C(C#N)C#N)C=C(C)O2)c(O)c1Cl]

and it was named CF-Cl-DPY-1. $^1$H NMR (400 MHz, CDCl$_3$, ppm): δ 7.66 (d, 1H, J=16.0 Hz, -Alkene-H), 7.39 (d, 1H, J=8.0 Hz, -Ph-H), 6.94 (d, 1H, J=16.0 Hz, -Alkene-H), 6.91 (d, 1H, J=8.0 Hz, -Ph-H), 6.71 (s, 1H, -Pyran-H), 6.56 (s, 1H, -Pyran-H), 6.28 (s, 1H, —OH), 3.33 (s, 3H, —O—CH$_3$), 3.28 (s, 1H, -Adamantane-H), 2.43 (s, 3H, —CH$_3$), 2.14 (s, 1H, -Adamantane-H), 1.97-1.77 (m, 12H, -Adamantane-H). $^{13}$C NMR (100 MHz, CDCl$_3$, ppm): δ 158.32, 155.95, 150.45, 139.33, 136.73, 132.54, 123.99, 123.88, 122.11, 121.66, 120.10, 115.22, 107.65, 60.07, 57.45, 39.16, 37.01, 32.98, 29.76, 28.24. Mass spectrometry (ESI-MS, m/z): [M−H]− calcd for C$_{29}$H$_{26}$ClN$_2$O$_3$, 485.1632; found, 485.1641.

0.08 mmol CF-Cl-DPY-1, 0.13 mmol triethylamine (TEA) and 20 mL ultra-dry tetrahydrofuran were added to a 100 mL dry bottle with two necks, and mixed evenly, the reaction solution changed from orange to red, and it was cooled to 0° C. Under the protection of ice bath and argon, 0.12 mmol of 4-nitrobenzyl chloroformate was dropped into the bottle with two necks, afterwards, it was naturally rise to 25° C. and stirred for 24 hours for a reaction. After the reaction was completed, the solvent was vacuum evaporated, and a yellow solid (18 mg, yield 34%) was obtained by column chromatography, that was a luminescent probe 1, with a structural formula

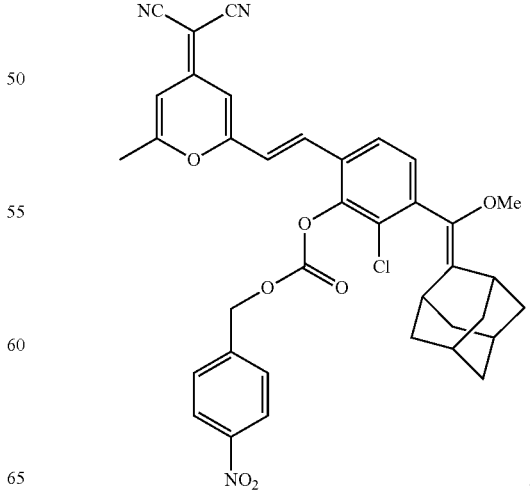

The synthetic route of the luminescent probe 1 was:

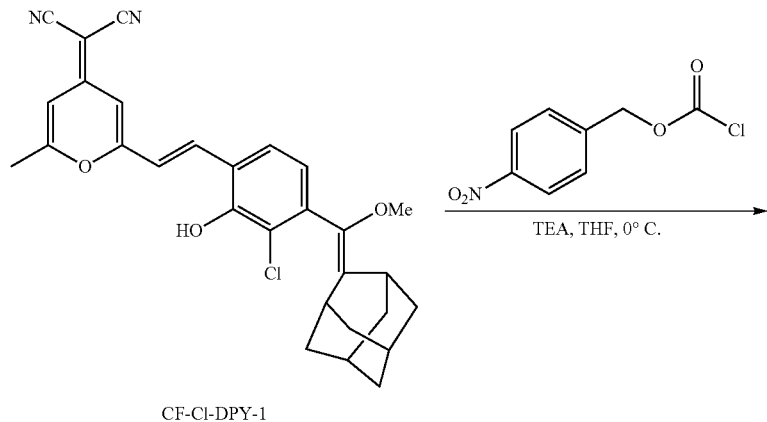

CF-Cl-DPY-1

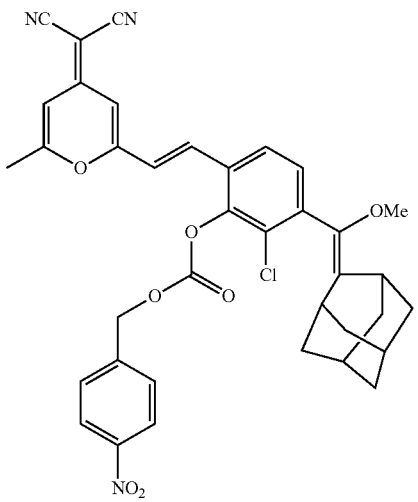

$^1$H-NMR (400 MHz, CDCl$_3$, ppm): δ 8.24 (d, 2H, J=8.4 Hz, -Ph-H), 7.62 (d, 2H, J=8.4 Hz, -Ph-H), 7.54 (d, 1H, J=8.0 Hz, -Ph-H), 7.45 (d, 1H, J=16.4 Hz, -Alkene-H), 7.30 (d, 1H, J=8.0 Hz, -Ph-H), 6.80 (d, 1H, J=16 Hz, -Alkene-H), 6.69 (s, 1H, -Pyran-H), 6.56 (s, 1H, -Pyran-H), 5.43 (s, 2H, —CH$_2$—), 3.32 (s, 3H, —O—CH$_3$), 3.28 (s, 1H, -Adamantane-H), 2.38 (s, 3H, —CH$_3$), 2.10 (s, 1H, -Adamantane-H), 1.97-1.72 (m, 12H, -Adamantane-H). $^{13}$C-NMR (100 MHz, CDCl$_3$, ppm): δ 171.22, 162.21, 157.98, 155.92, 151.81, 148.08, 145.62, 141.44, 138.69, 138.12, 133.89, 130.13, 129.09, 128.73, 126.99, 125.19, 123.93, 123.68, 122.07, 114.74, 108.54, 106.65, 69.41, 63.88, 60.49, 57.50, 38.59, 36.94, 32.94, 29.79, 28.24, 21.07, 20.00, 14.20. Mass spectrometry (ESI-MS, m/z): [M−H]− calcd for C$_{37}$H$_{31}$ClN$_3$O$_7$, 664.1845; found, 664.1867.

Embodiment 2

Embodiment 2 was the same as step (1) of Embodiment 1, firstly, the phenolic hydroxyl precursor (CF-Cl-DPY-1) was prepared.

0.064 mmol CF-Cl-DPY-1, 0.10 mmol cesium carbonate and 20 mL ACN were added to a 50 mL dry bottle with two necks and cooled to 0° C., subsequently, 0.13 mmol of 4-nitrobenzyl bromide was added dropwise and reacted for 20 h. After the reaction was completed, the mixture was diluted with 100 mL of ethyl acetate (EA), washed with 100 mL of saturated ammonium chloride solution, dried with anhydrous sodium sulfate, subjected to reduced pressure distillation, and purified by column chromatography, a yellow solid (17 mg, yield 43%) was obtained, that was a luminescent probe 2, with a structural formula

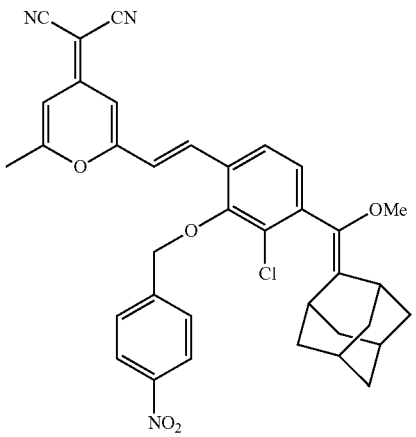 [SMILES: COC(=C1C2CC3CC(C2)CC1C3)c1ccc(/C=C/C2=CC(=C(C#N)C#N)C=C(C)O2)c(OCc2ccc([N+](=O)[O-])cc2)c1Cl]

The synthetic route of the luminescent probe 2 was:

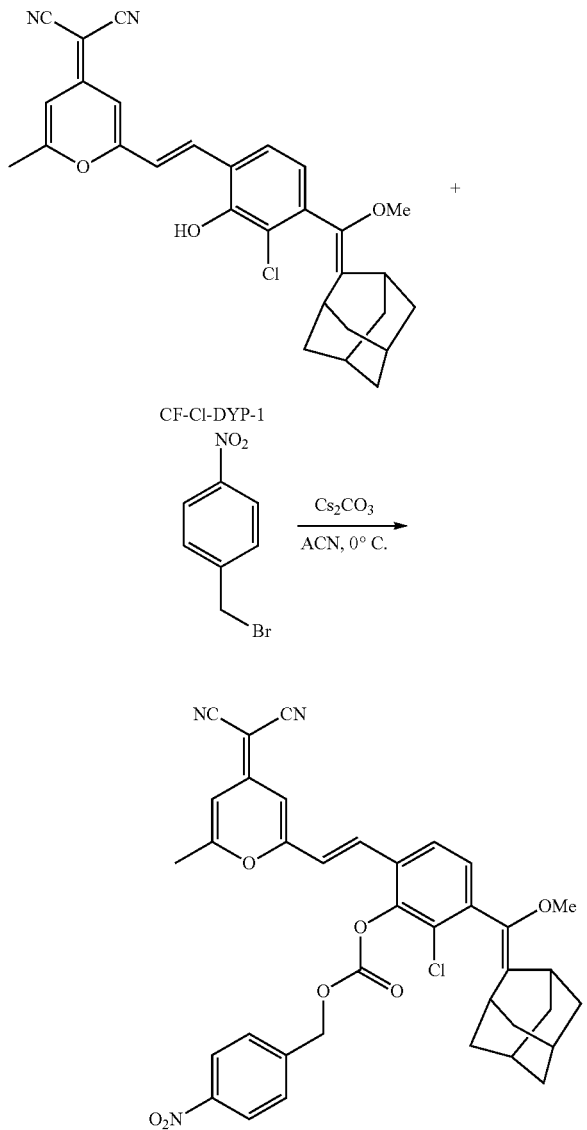

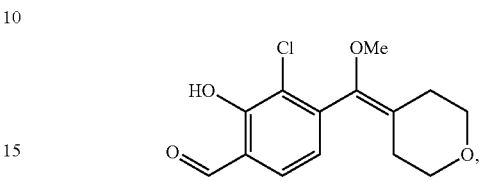

¹H-NMR (400 MHz, CDCl₃, ppm): δ 8.29 (d, 2H, J=8.4 Hz, -Ph-H), 7.70 (d, 2H, J=7.6 Hz, -Ph-H), 7.61 (d, 1H, J=15.2 Hz, -Alkene-H), 7.51 (d, 1H, J=8.4 Hz, -Ph-H), 7.18 (d, 1H, J=8 Hz, -Ph-H), 6.75 (d, 1H, J=16 Hz, -Alkene-H), 6.66 (s, 1H, -Pyran-H), 6.54 (s, 1H, -Pyran-H), 5.14 (d, 2H, J=5.6 Hz, —CH₂—), 3.36 (s, 3H, —O—CH3), 3.30 (s, 1H, -Adamantane-H), 2.31 (s, 3H, —CH3), 2.11 (s, 1H, -Adamantane-H), 1.98-1.73 (m, 12H, -Adamantane-H). ¹³C-NMR (100 MHz, CDC₃, ppm): δ 161.86, 158.30, 155.93, 153.29, 147.93, 143.43, 139.20, 138.58, 133.40, 131.06, 129.68, 129.40, 128.38, 124.60, 123.85, 120.54, 114.74, 108.10, 106.60, 74.46, 60.43, 57.50, 38.72, 36.99, 33.05, 29.78, 28.18, 19.92. Mass spectrometry (ESI-MS, m/z): [M+Na]+ calcd for C₃₆H₃₂ClN₃O₅Na, 644.1928; found, 644.1925.

Embodiment 3

2.48 mmol 4-(dicyanomethylene)-2,6-dimethyl-4H-pyran, 2.48 mmol compound 1, 25 mL acetonitrile and 0.5 mL piperidine were added to a 100 mL dry bottle with two necks, after mixing evenly, the reaction was performed at 25° C. for 6 h, after cooling, the organic solvent was removed by vacuum concentration, the crude solid obtained is purified by silica gel column chromatography, a yellowish-brown solid (130 mg, yield 12.03%) was obtained, that was a phenolic hydroxyl precursor, wherein compound 1 was a

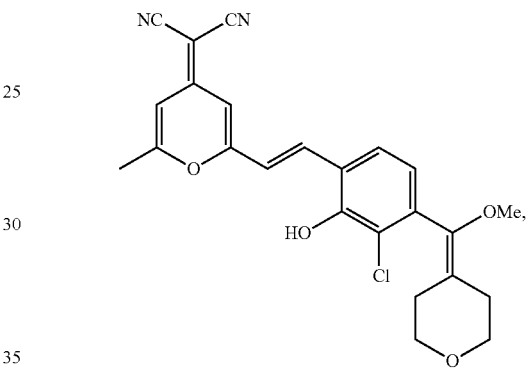

a structural formula of the phenolic hydroxyl precursor obtained was and it was named CF-Cl-DPY-2.

¹H NMR (400 MHz, CDCl₃, ppm): δ 7.65 (d, 1H, J=16.4 Hz, -Alkene-H), 7.42 (d, 1H, J=8.0 Hz, -Ph-H), 6.95 (d, 1H, J=16.4 Hz, -Alkene-H), 6.93 (d, 1H, J=8.0 Hz, -Ph-H), 6.72 (d, 1H, J=2.0 Hz, -Pyran-H), 6.56 (d, 1H, J=1.2 Hz, -Pyran-H), 6.30 (s, 1H, -Hydroxyl-H), 3.77-3.74 (m, 2H, -Pyran-H), 3.63-3.61 (m, 2H, -Pyran-H), 3.32 (s, 3H, —O—CH₃), 2.57 (m, 2H, -Pyran-H), 2.43 (s, 3H, —CH₃), 2.01-1.98 (m, 2H, -Pyran-H). ¹³C NMR (100 MHz, CDCl₃, ppm): δ 162.15, 159.02, 156.29, 150.32, 143.89, 135.54, 132.07, 126.67, 123.82, 122.51, 121.52, 120.60, 119.63, 114.95, 107.86, 106.55, 68.60, 59.66, 57.00, 30.27, 27.48. Mass spectrometry (ESI-MS, m/z): [M−H]− calcd for C24H20ClN2O, 435.1106; found, 435.1118.

0.12 mmol CF-PY-DPY-2, 0.19 mmol triethylamine (TEA) and 20 mL ultra-dry tetrahydrofuran were added to a 100 mL dry bottle with two necks, after mixing evenly, the reaction solution changed from orange to red, and it was cooled to 0° C. Under the protection of ice bath and argon, 0.18 mmol of 4-nitrobenzyl chloroformate was dropped into the reaction bottle, after 24 hours of reaction, the solvent was vacuum evaporated, and a yellow solid (26 mg, yield 35%) was obtained by column chromatography, that was a luminescent probe 3, with a structural formula

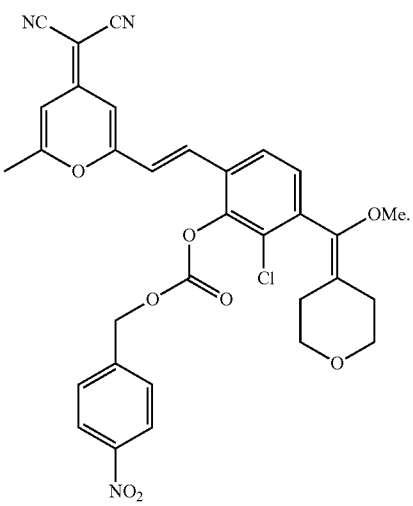 [SMILES: COC(=C1CCOCC1)c1ccc(/C=C/C2=CC(=C(C#N)C#N)C=C(C)O2)c(OC(=O)OCc2ccc([N+](=O)[O-])cc2)c1Cl]

The synthetic route of the luminescent probe 3 was:

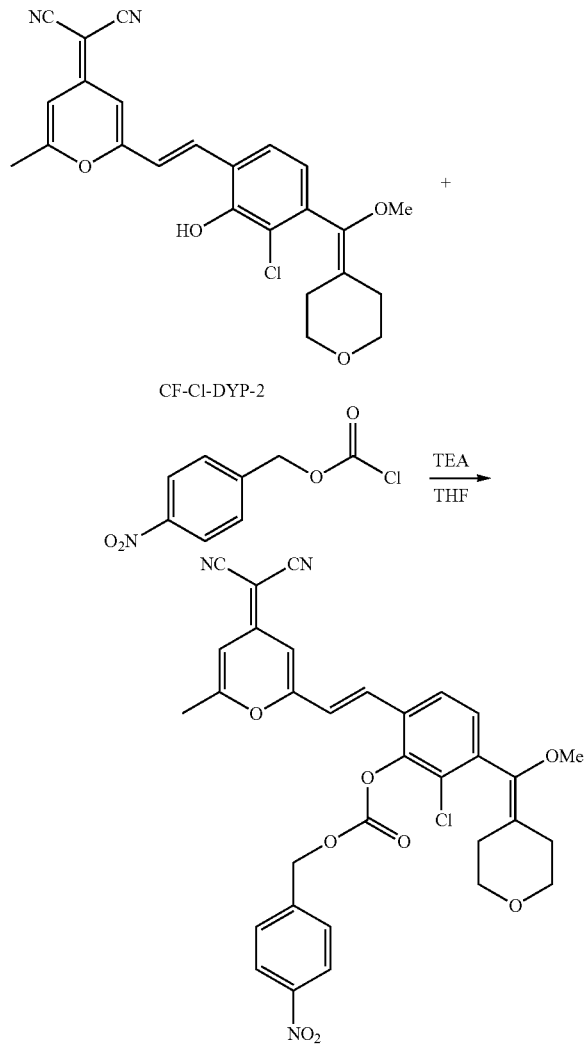

$^1$H-NMR (400 MHz, CDCl$_3$, ppm): δ 8.25 (d, 2H, J=8.8 Hz, -Ph-H), 7.62 (d, 2H, J=8.8 Hz, -Ph-H), 7.55 (d, 1H, J=8.0 Hz, -Ph-H), 7.42 (d, 1H, J=16.4 Hz, -Alkene-H), 7.31 (d, 1H, J=8.0 Hz, -Ph-H), 6.78 (d, 1H, J=16.4 Hz, -Alkene-H), 6.69 (s, 1H, -Pyran-H), 6.56 (s, 1H, -Pyran-H), 5.43 (s, 2H, —CH$_2$—), 3.76-3.64 (t, 2H, -Pyran-H), 3.62-3.59 (m, 2H, -Pyran-H), 3.31 (s, 3H, —O—CH$_3$), 2.60-2.50 (m, 2H, -Pyran-H), 2.37 (s, 3H, —CH$_3$), 2.00-1.96 (m, 2H, -Pyran-H). $^{13}$C-NMR (100 MHz, CDCl$_3$, ppm): δ 162.00, 157.73, 155.72, 151.82, 148.19, 145.60, 143.20, 141.28, 137.12, 130.03, 129.64, 129.21, 129.14, 128.74, 125.46, 123.97, 122.47, 120.43, 114.44, 108.67, 106.68, 69.48, 68.46, 61.01, 57.09, 30.21, 27.48, 19.95. Mass spectrometry (ESI-MS, m/z): [M—H]- calcd for C$_{32}$H$_{25}$ClN$_3$O$_8$, 614.1325; found, 614.1330.

Application Example 1

Figure 1A:
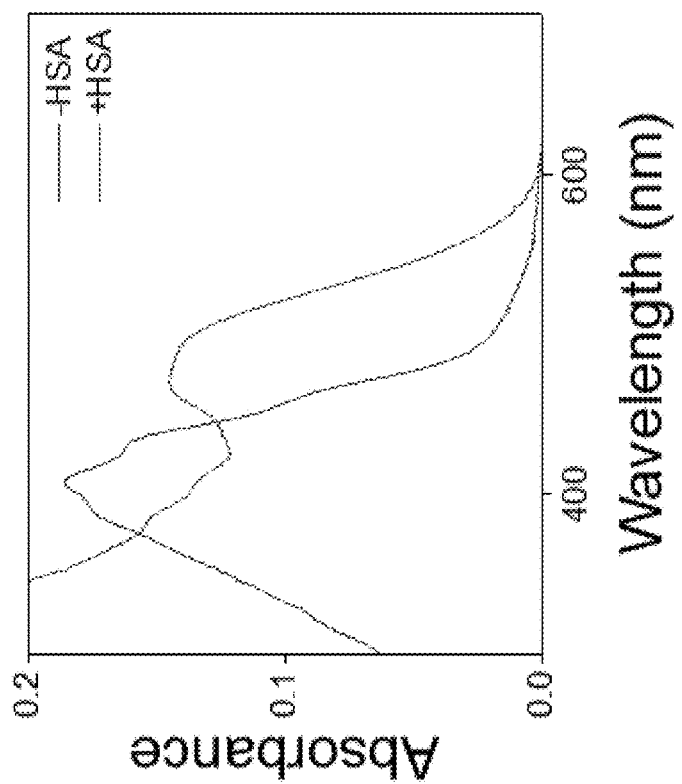

The luminescent probe 1 prepared in Embodiment 1 was dissolved in dimethyl sulfoxide to prepare a luminescent probe stock solution with a concentration of $1.0 \times 10^{-3}$ M, the HSA solid was dissolved in dimethyl sulfoxide to prepare a HSA stock solution with a concentration of $1.0 \times 10^{-2}$ M. 0.6 mL dimethyl sulfoxide and 1.4 mL PBS buffer solution (pH 7.4) were taken to prepare a 2 mL mixed solvent, then 20 μL of the luminescent probe stock solution was added to the mixed solvent, after mixing evenly, the product was transferred to an optical quartz cuvette (10×10 mm) to test its absorption and fluorescence spectra, as shown in FIGS. 1A and 1B, the maximum absorption wavelength before response was at 400 nm. Then 20 μL of HSA stock solution was added to the cuvette and incubated at 37° C. for 44 min, the absorption and fluorescence spectra were tested, the maximum absorption wavelength after response was at 495 nm, and the fluorescence spectrum with the maximum emission wavelength of 615 nm was obtained by excitation at this wavelength.

Application Example 2

Figures 2A, 2B, 2C:
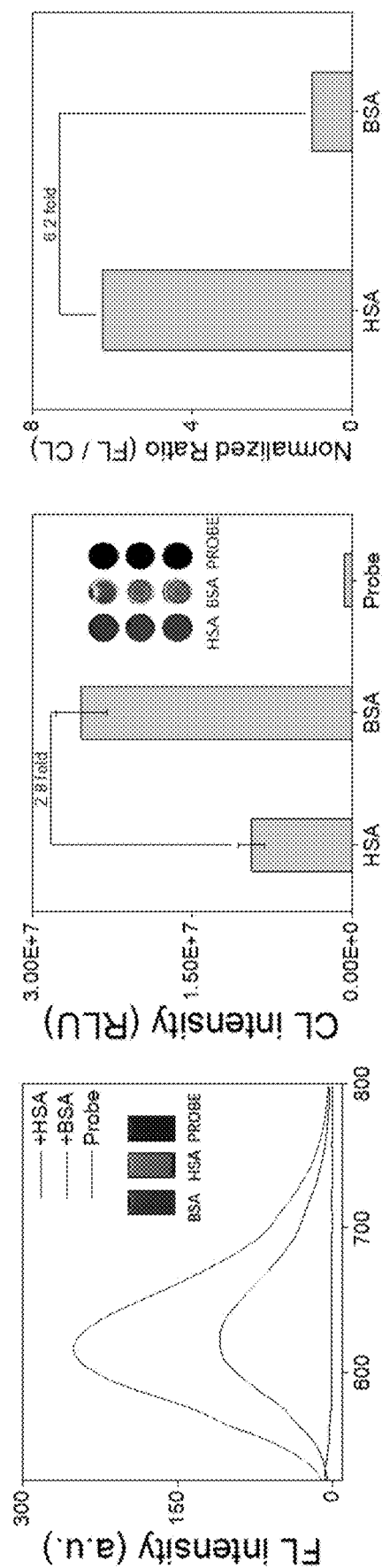

The luminescent probe 1 prepared by Embodiment 1 was dissolved in dimethyl sulfoxide, to prepare a luminescent probe reserve solution with a concentration of $1.0 \times 10^{-3}$ M. HSA solid and BSA solid were dissolved in dimethyl sulfoxide, respectively, to prepare an HSA stock solution and a BSA stock solution with a concentration of both $2.0 \times 10^{-3}$M. Two portions of mixed solvent were prepared according to the volume ratio of dimethyl sulfoxide to PBS buffer solution of 0.6 mL:1.4 mL, and the pH of PBS buffer solution was 7.4. Then, two portions of 20 μL of the luminescent probe stock solution were added to 2 mL of the mixed solvent, respectively, after mixing evenly, two products were transferred to two optical quartz colorimetric dishes (10×10 mm), then 20 μL of HSA stock solution and 20 μL of BSA stock solution were taken, respectively, and added to the two optical quartz colorimetric dishes, being incubated at 37° C. for 44 minutes, after being mixed evenly, the absorption and fluorescence spectra and chemiluminescence intensity were tested, and the results were shown in FIGS. 2A-2C. It could be seen from the fluorescence spectrum of FIGS. 2A-2C that the signal after incubation with HSA stock solution was about twice that of BSA stock solution, It could be seen from the chemiluminescence intensity diagram of FIGS. 2A-2C that, contrary to the fluorescence spectrum, the signal after incubation with BSA stock solution was about 2.8 times that of HSA stock solution. It was worth noting that after the two signals were normalized respectively, the difference between the two was more significant by dividing the fluorescence signal by the chemiluminescence signal, and the HSA group was about 6.2 times that of the BSA group (referring to the normalized ratio comparison chart of fluorescence intensity and chemiluminescence intensity in FIGS. 2A-2C).

Application Example 3

The luminescent probe 1 prepared by Embodiment 1 was dissolved in dimethyl sulfoxide, to prepare a luminescent probe reserve solution with a concentration of $1.0 \times 10^{-3}$ M, HSA solid was dissolved in dimethyl sulfoxide to prepare an HSA stock solution with a concentration of $2.0 \times 10^{-4}$ M. According to the volume ratios of dimethyl sulfoxide and PBS buffer solution, wherein they were 0.6 mL:1.24 mL, 0.6 mL:1.26 mL, 0.6 mL:1.28 mL, 0.6 mL:1.30 mL, 0.6 mL:1.32 mL, 0.6 mL:1.34 mL, 0.6 m:1.36 mL, 0.6 mL:1.38 mL, respectively, the mixed solvents were prepared, 20 μL of the fluorescent probe stock solution was mixed evenly with the mixed solvent, and then the HSA stock solution was added to keep the concentration of HSA between 0~3.5 μM, after being mixed evenly, being incubated at 37° C. for 44 minutes, and the fluorescence spectrum of the fluorescence signal increased linearly with the concentration of HSA was measured. Subsequently, the series of test solutions were subjected to a chemiluminescence test, and illuminated with a flashlight with an excitation light intensity of 21 mW·cm$^{-2}$ for 3 s, immediately, the Imaging Quant 4000 system was used to collect images, then, after quantitative processing of the collected images, it was found that the chemiluminescence signal increased linearly with the concentration of HSA. From FIGS. 3A and 3B, it could be seen that when HSA was added, the linear relationship diagram of the fluorescence signal showed $R^2$=0.990, LODFL=10.5 nM, and the linear relationship diagram of the chemiluminescence signal showed $R^2$=0.851, LODCL=8.21 nM.

Application Example 4

Figure 3B:
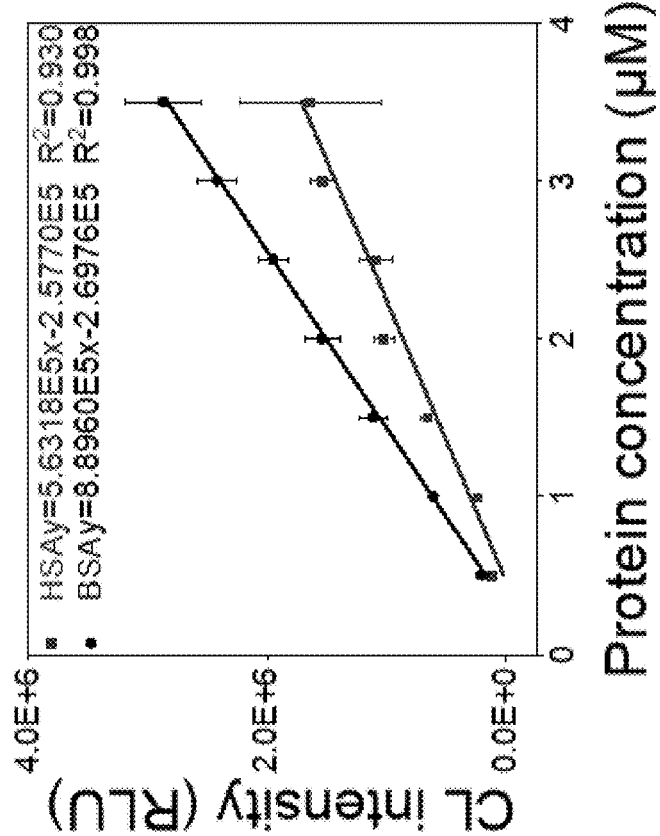
Figure 3A:
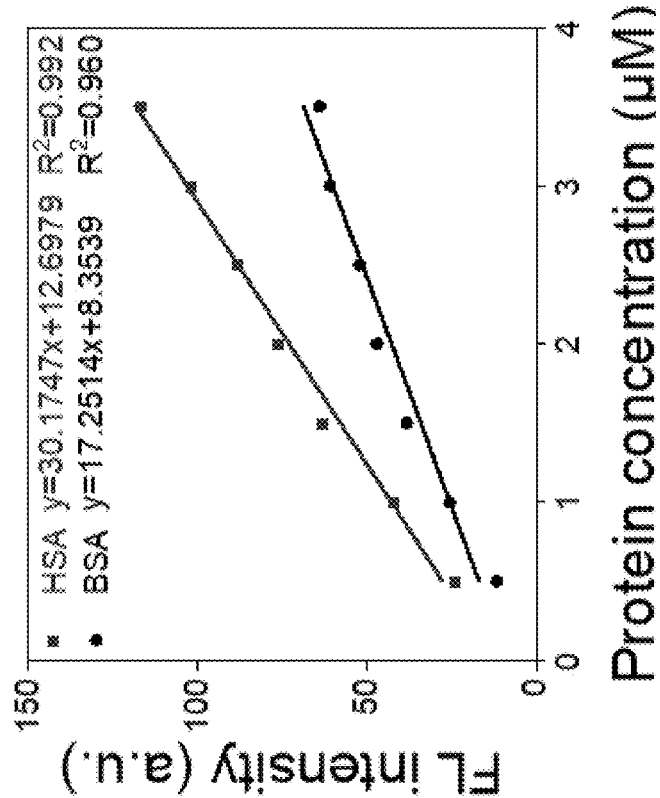

The luminescent probe 1 prepared by Embodiment 1 was dissolved in dimethyl sulfoxide to prepare a luminescent probe reserve solution with a concentration of $1.0 \times 10^{-3}$ M, and the BSA solid was dissolved in dimethyl sulfoxide to prepare a BSA stock solution with a concentration of $2.0 \times 10^{-4}$ M. According to the volume ratios of dimethyl sulfoxide and PBS buffer solution, wherein they were 0.6 mL:1.24 mL, 0.6 mL:1.26 mL, 0.6 mL:1.28 mL, 0.6 mL:1.30 mL, 0.6 mL:1.32 mL, 0.6 mL:1.34 mL, 0.6 mL:1.36 mL, 0.6 mL:1.38 mL, respectively, the mixed solvents were prepared, 20 μL of the luminescent probe stock solution was mixed evenly with the mixed solvent, and then the BSA stock solution was added to keep the concentration of BSA between 0~3.5 μM, after being mixed evenly, being incubated at 37° C. for 44 minutes, and the fluorescence spectrum of the fluorescence signal increased linearly with the concentration of BSA was measured. Subsequently, the series of test solutions were subjected to a chemiluminescence test, and illuminated with a flashlight with an excitation light intensity of 21 mW·cm$^{-2}$ for 3 s, immediately, the Imaging Quant 4000 system was used to collect images, then, after quantitative processing of the collected images, it was found that the chemiluminescence signal increased linearly with the concentration of BSA, as shown in FIGS. 3A and 3B. It could be seen from FIGS. 3A and 3B that when BSA was added, the linear relationship diagram of the fluorescence signal showed $R^2$=0.967, LODFL=17.41 nM, and the linear relationship diagram of the chemiluminescence signal showed $R^2$=0.967, LODFL=17.41 nM.

Application Example 5

The luminescent probe 1 prepared by Embodiment 1 was dissolved in dimethyl sulfoxide to prepare a luminescent probe reserve solution with a concentration of $1.0 \times 10^{-3}$ M, HSA and BSA were dissolved in dimethyl sulfoxide, respectively, to prepare an HSA stock solution and a BSA stock solution with a concentration of both $2.0 \times 10^{-4}$ M. The mixed solvent was prepared according to the volume ratio of dimethyl sulfoxide and PBS buffer solution (pH 7.4) of 0.6 mL:1.2 mL, a total of 11 portions. Then 11 portions of 20 μL luminescent probe stock solution and mixed solvent were mixed evenly, then a mixed solution was added, being incubated at 37° C. for 44 min, a solution to be tested was obtained, wherein the mixed solution was composed of HSA stock solution and BSA stock solution, the volume dosage of HSA stock solution and BSA stock solution is shown in Table 1, [HSA]+[BSA]=20 μM.

Figure 4A:
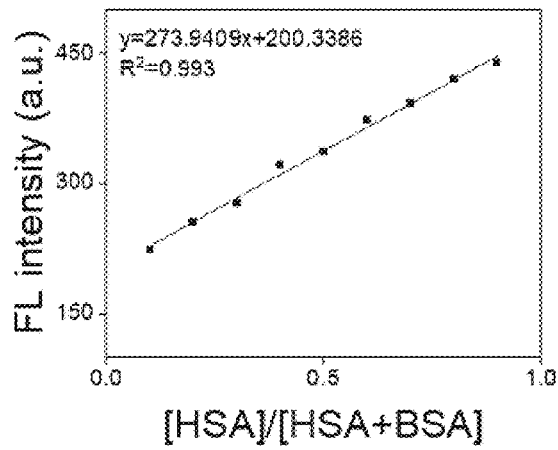
Figure 4B:
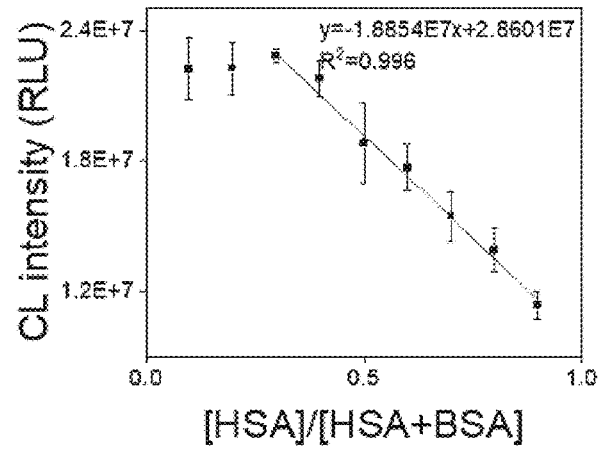
Figure 4C:
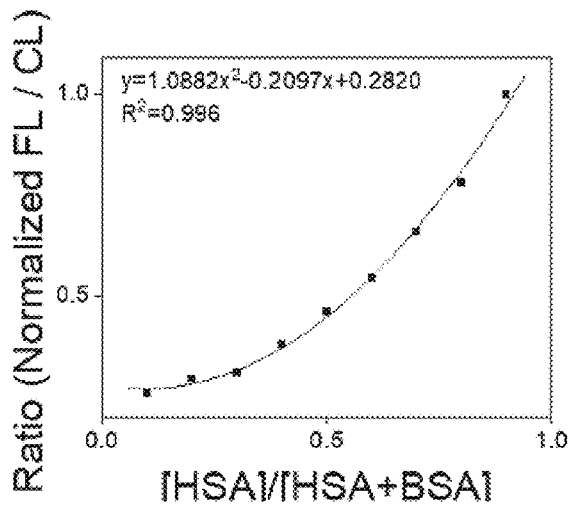

The fluorescence spectrum of the solution to be tested of the fluorescence signal increasing linearly with the ratio of [HSA]/[HSA+BSA] was determined (as shown in FIGS. 4A-4C). The series of solutions to be tested were subjected to a chemiluminescence test, and illuminated with a flashlight with an excitation light intensity of 21 mW·cm$^{-2}$ for 3 s, immediately, the Imaging Quant 4000 system was used to collect images, then, after quantitative processing of the collected images, it was found that the chemiluminescence signal decreased linearly with the ratio of [HSA]/[HSA+BSA], as shown in FIGS. 4A-4C. In FIGS. 4A-4C, the linear relationship diagram of the fluorescence signal showed $R^2$=0.993, and the linear relationship diagram of the chemiluminescence signal showed $R^{20}$=0.996.

TABLE 1

| Volume Dosage of HSA Stock Solution and BSA Stock Solution | | | | | | | | | | | |
|---|---|---|---|---|---|---|---|---|---|---|---|
| Types of Stock Solution | Dosage (μL) | | | | | | | | | | |
| HSA Stock Solution | 200 | 180 | 160 | 140 | 120 | 100 | 80 | 60 | 40 | 20 | 0 |
| BSA Stock Solution | 0 | 20 | 40 | 60 | 80 | 100 | 120 | 140 | 160 | 180 | 200 |

Figure 5B:
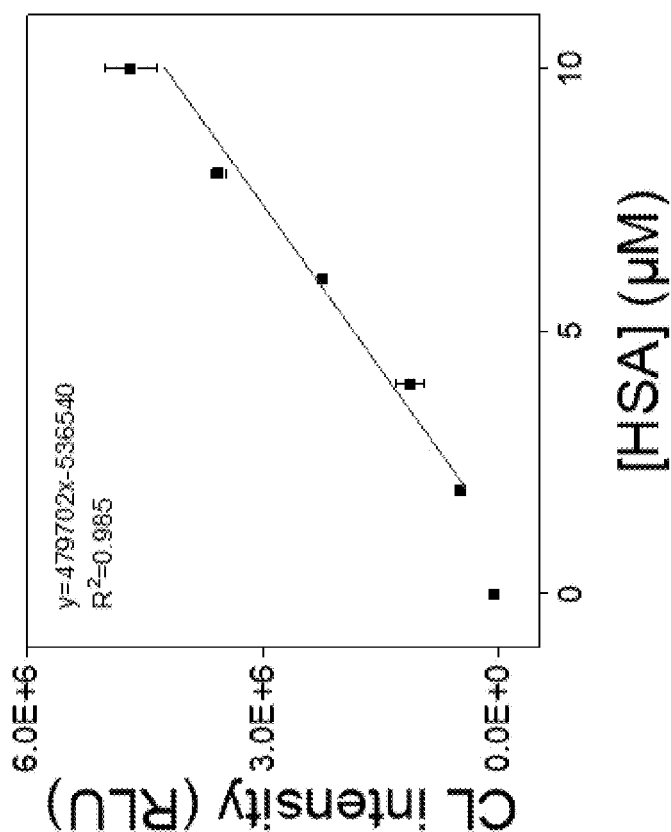
Figure 5A:
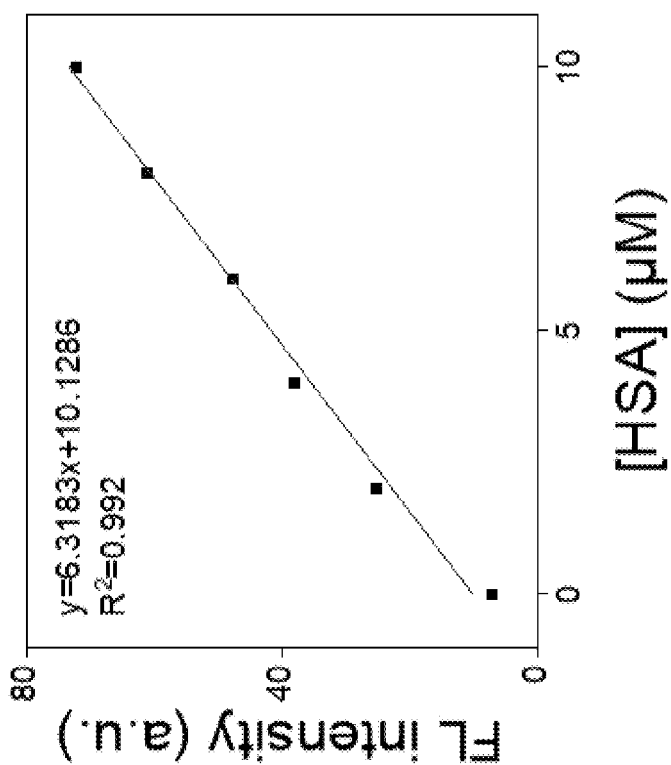

Performance Verification (1) The luminescent probe 1 prepared in Embodiment 1 was dissolved in dimethyl sulfoxide to prepare a $1.0\times10^{-3}$ M luminescent probe stock solution, and the HSA solid was dissolved in dimethyl sulfoxide to prepare a $1.0\times10^{-3}$ M HSA stock solution. Five portions of mixed solvent were prepared according to the volume ratio of dimethyl sulfoxide, Tris-HCl (pH=8.8) and unpretreated healthy human urine of 0.6 mL:0.7 mL:0.7 mL, then 5 portions of 20 μL luminescent probe stock solution were mixed with mixed solvent, afterwards, after adding HSA stock solution. respectively, being incubated at 37° C. for 44 minutes, a solution to be tested was obtained, the concentrations of HSA in the solution to be tested were 0 μM, 2 μM, 4 μM, 6 μM, 8 μM, and 10 μM, and the fluorescence spectra of the solution to be tested with increasing HSA concentration were measured. The series of solutions to be tested were subjected to a chemiluminescence test, and illuminated with a flashlight with an excitation light intensity of 21 mW·cm$^{-2}$ for 3 s, immediately, the Imaging Quant 4000 system was used to collect images, then, after quantitative processing of the collected images, it was found that the chemiluminescence signal increased linearly with the concentration of HSA (as shown in FIGS. 5A and 5B). In FIGS. 5A and 5B, the linear relationship diagram of the fluorescence signal showed $R^2=0.992$, LODFL=0.202 μM, and the linear relationship diagram of the chemiluminescence signal showed $R^2=0.985$, LODCL=0.648 μM.

(2) Confocal imaging of fluorescent probes in Hepg2 cells after incubation with HSA and BSA, respectively: human hepatoellular carcinomas cells (Hepg 2 cell) were purchased from the Shanghai Institute of Cell Biology. DMEM cell culture medium was cultured at 37° C. in a humidified atmosphere containing 5% $CO_2$.

Figure 6:
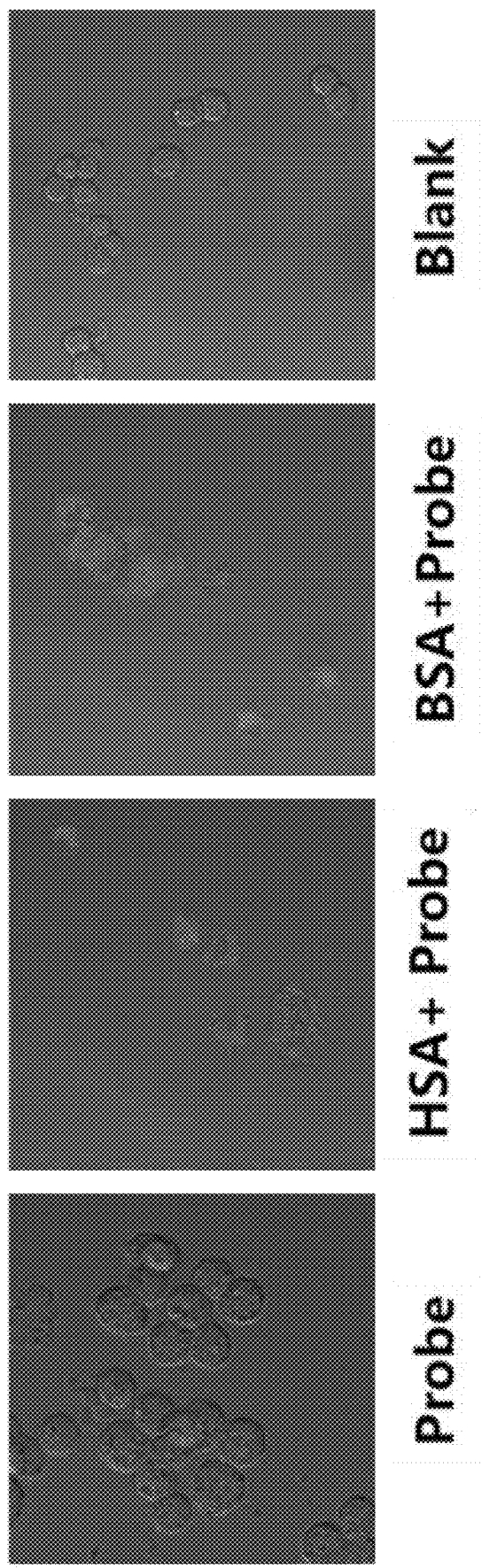
FIG. 6 shows the confocal imaging of the luminescent probe 1 prepared by Embodiment 1 after incubation with HSA and BSA in Hepg2 cells, respectively.
Figure 7:
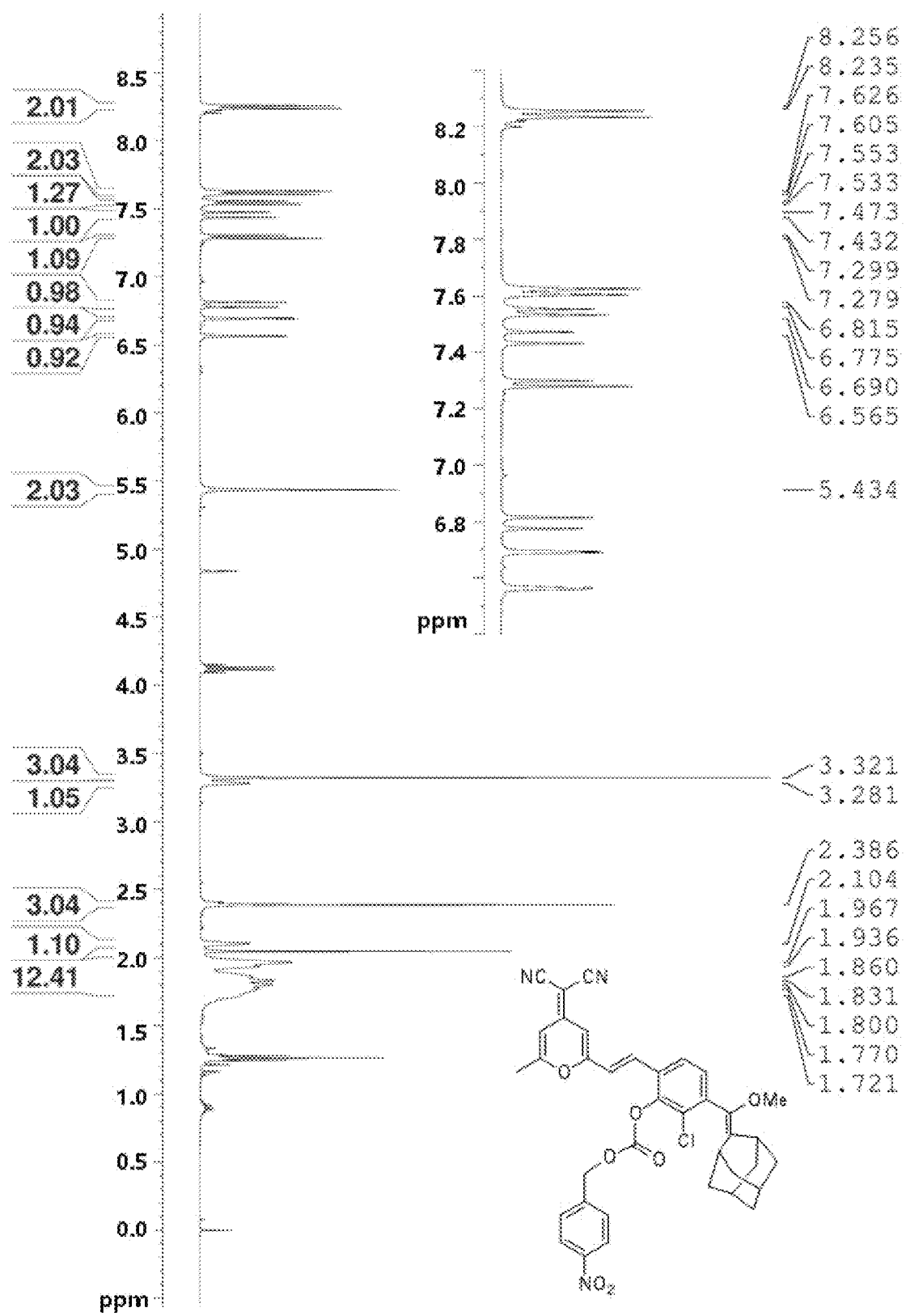
FIG. 7 is a nuclear magnetic resonance hydrogen spectrum of the luminescent probe 1 prepared by Embodiment 1.
Figure 8:
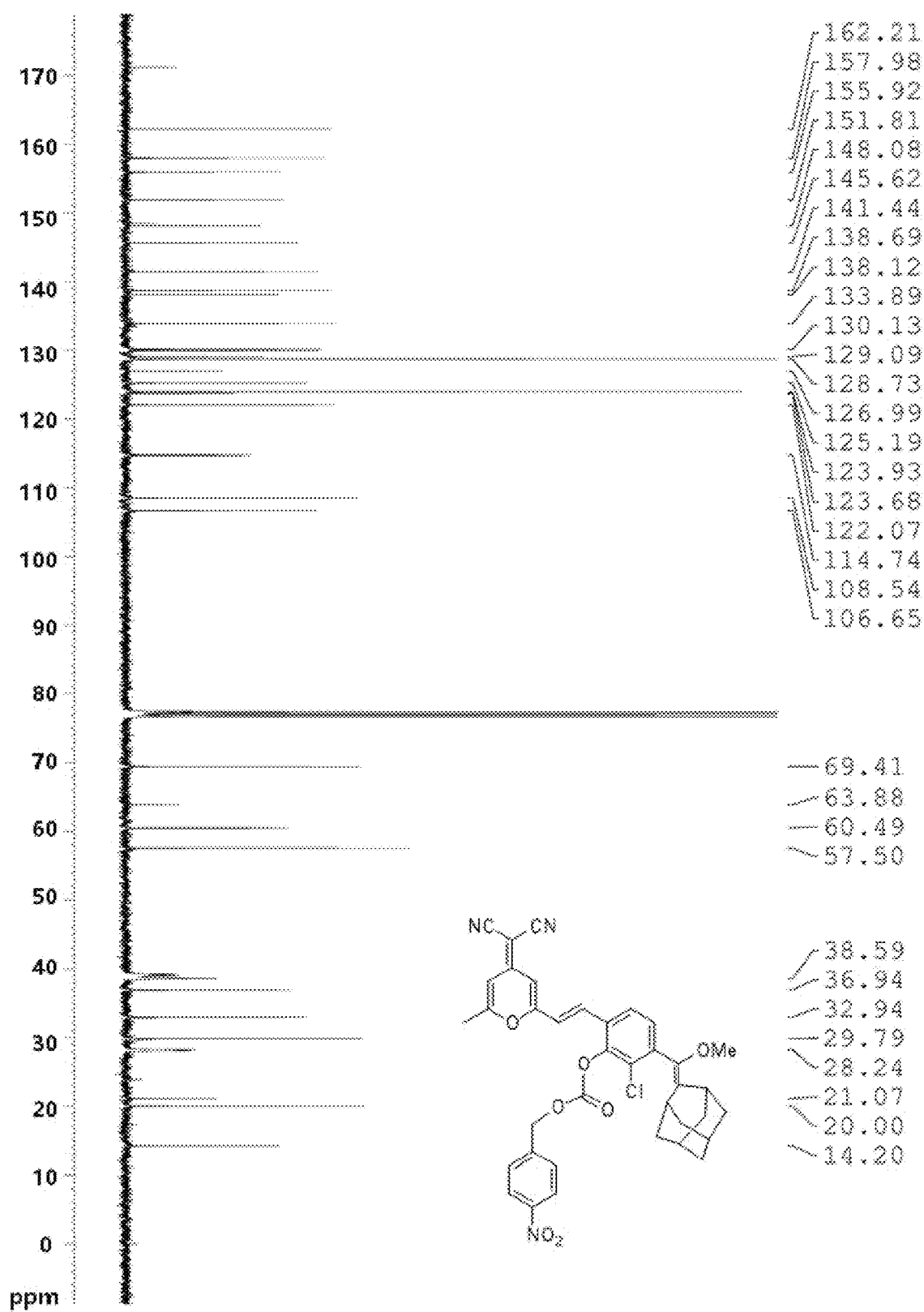
FIG. 8 is a carbon spectrum of the luminescent probe 1 prepared by Embodiment 1.
Figure 9:
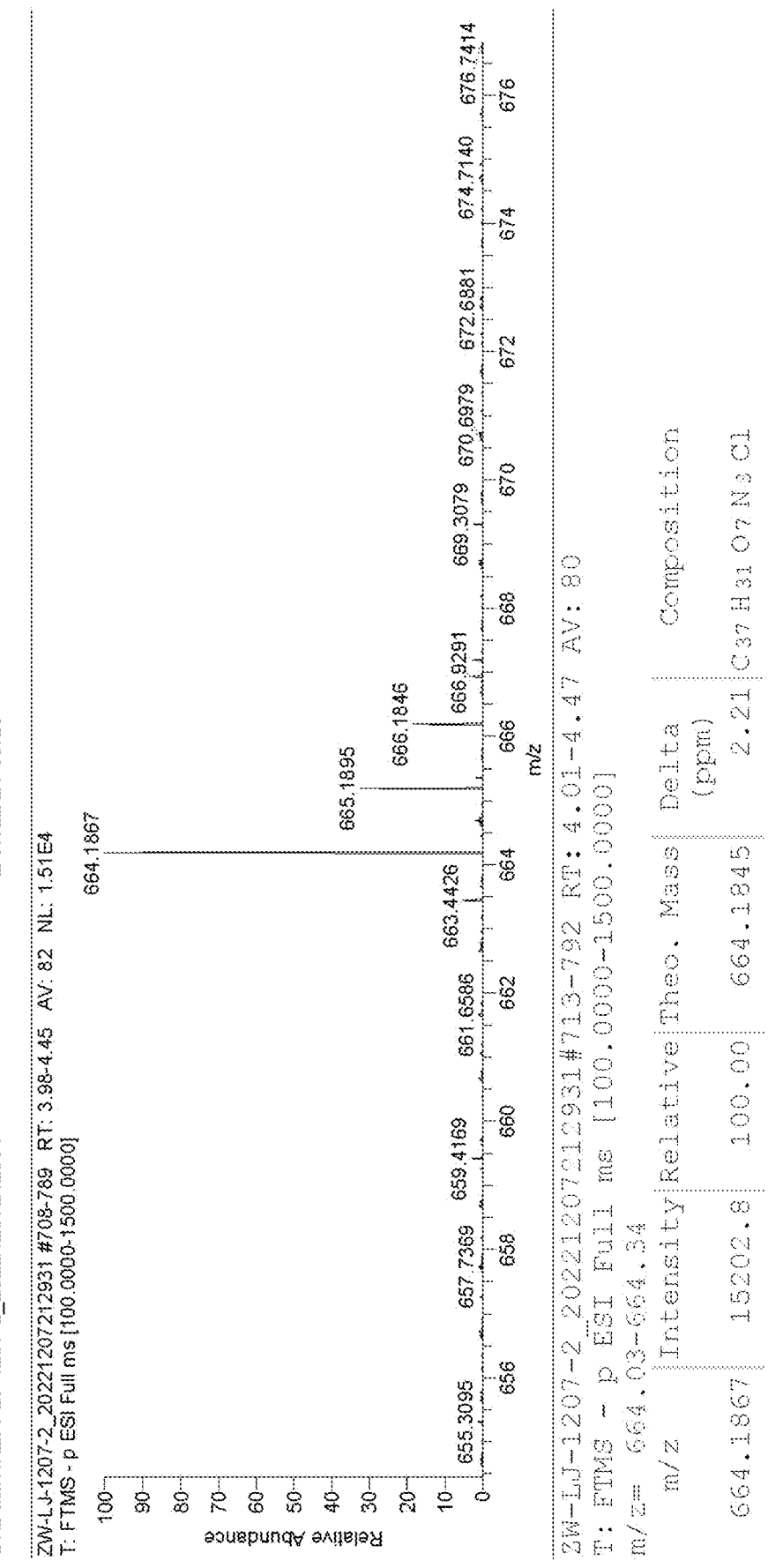
FIG. 9 is a high resolution mass spectrum of the luminescent probe 1 prepared by embodiment 1.

Hepg2 cells were transferred at a density of $1\times10^5$ cells/well into a glass culture dish containing 1.5 mL complete medium, after full adherence, 200 μg/mL HSA stock solution or 200 μg/mL BSA stock solution was added, being incubated at 37° C. for 1 h, then the product was washed with PBS three times (1 mL×3), then DMEM medium containing 10 μM luminescent probe 1 was added, being incubating in dark for 1 h; after the incubation was completed, PBS was used to wash (1 mL×3), subsequently, imaging with a Leica confocal laser microscope Leica TCS SP8 (63×oil immersion lens). The excitation wavelength was 488 nm, and the fluorescence wavelength was 610-650 nm. As shown in FIG. 6, the cytoplasm added with HSA or BSA showed obvious red fluorescence, indicating that the chemiluminescence probe had good cell membrane permeability, and both HSA and BSA could activate the luminescent probe in a physiological environment.

It can be seen from the above embodiments that the present invention provides a luminescent probe and its preparation method and application. The luminescent probe of the invention has a steric hindrance group $R_1$ of aliphatic hydrocarbon structure such as adamantane or norborneol, a detection group $R_2$ of nitrobenzyl and its derivative structure, an electron-withdrawing group $R_3$ containing cyano group and an electron-donating group methoxy group, in the presence of HSA or BSA, the detection group is cut off to form a parent structure that exposes atomic oxygen anions and is activated under external light irradiation, the luminescent probe can be used in solution or cells, when detecting HSA or BSA, the luminescent probe has obvious chemiluminescence characteristics, which can sensitively distinguish HSA and BSA, quantitatively analyze HSA and BSA, and determine the mixing ratio of HSA and BSA at the same time, and the luminescent probe has been successfully used for cell fluorescence imaging.

The above is only a preferred embodiment of the present disclosure. It should be pointed out that for ordinary technical personnel in the art, several improvements and embellishments can be made without departing from the principles of the present disclosure, which should also be considered as the scope of protection of the present disclosure.

What is claimed is:

1. A luminescent probe, wherein the luminescent probe has a structural formula shown in formula (I)

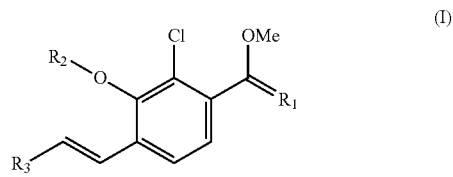

wherein $R_1$ is selected from one of

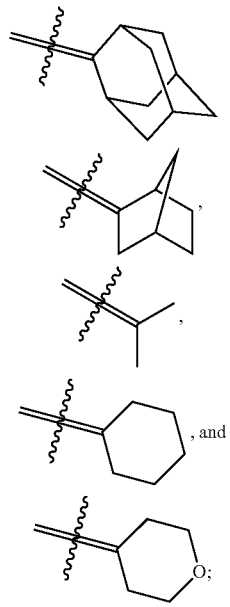

$R_2$ is selected from one of

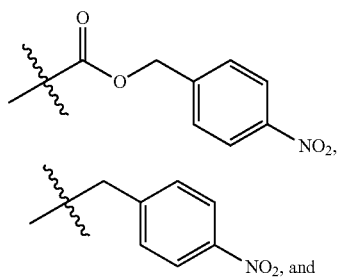

-continued
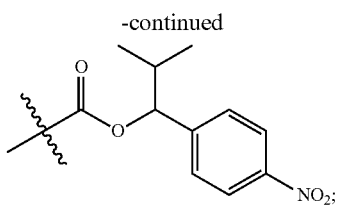
and R₃ is selected from one of
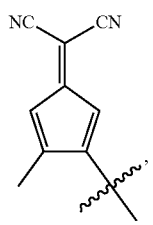
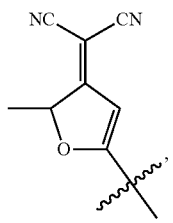
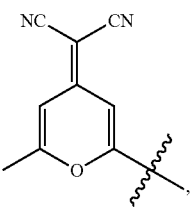
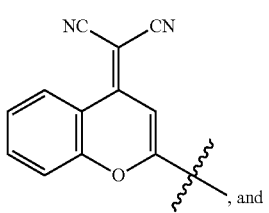
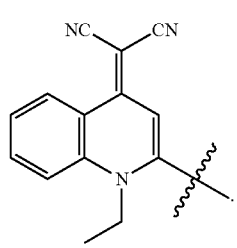
2. The luminescent probe according to claim 1, wherein the structural formula of the luminescent probe is
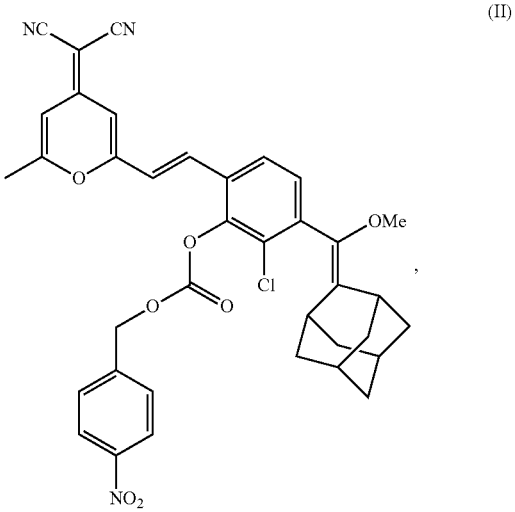
(II)
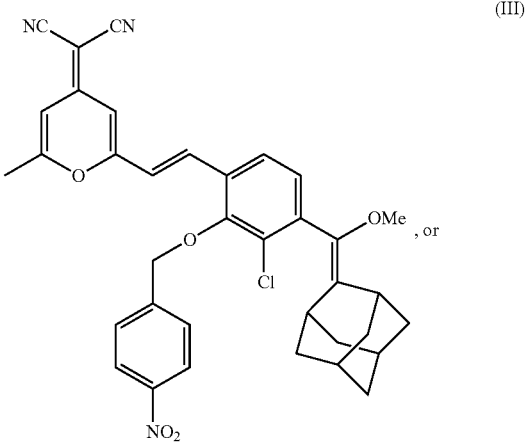
(III), or
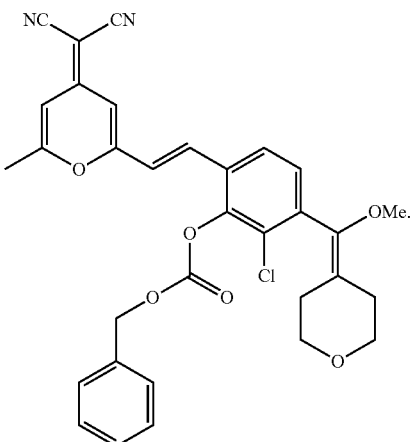
(IV)

3. A preparation method for a luminescent probe, wherein the luminescent probe has a structural formula shown in formula (I)

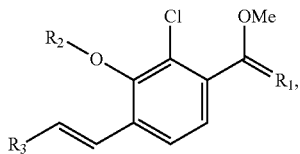

wherein $R_1$ is selected from one of

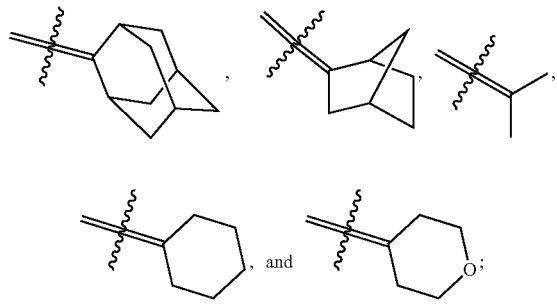

$R_2$ is selected from one of

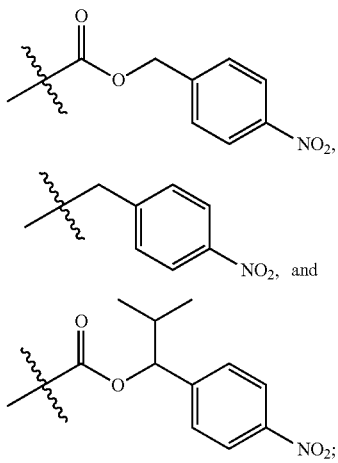

and $R_3$ is selected from one of

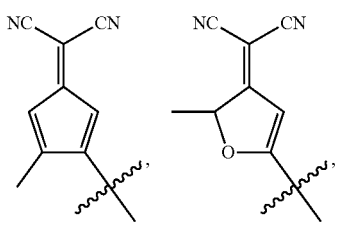

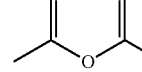

the preparation method comprising the following steps:
1) mixing 4-(dicyanomethylene)-2, 6-dimethyl-4H-pyran, a first compound, acetonitrile, and piperidine, then performing a first reaction, to obtain a phenolic hydroxyl precursor;
2) mixing the phenolic hydroxyl precursor, a second compound, and a solvent, then cooling to 0° C., adding nitro compounds, and performing a second reaction, to obtain the luminescent probe with the structural formula (II), (III) or (IV);

in step 1), the first compound is

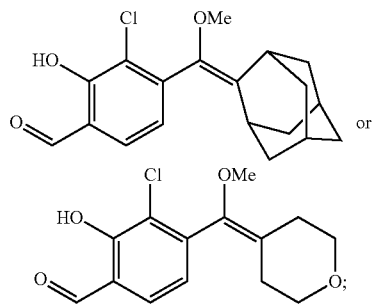

and
in step 2), the second compound is triethylamine or cesium carbonate; the nitro compounds are benzyl 4-nitrochloroformate or 4-nitrobenzyl bromide.

4. The preparation method according to claim 3, wherein in step 1), a molar volume ratio of the 4-(dicyanomethylene)-2, the 6-dimethyl-4H-pyran, the first compound, the acetonitrile, and the piperidine is 0.6-2.5 mmol:0.6-2.5 mmol:20-30 mL:0.1-1 mL.

5. The preparation method according to claim 3, wherein in step 1), a reaction temperature is 20-30° C., and a reaction time is 5-7 h.

6. The preparation method according to claim 5, wherein in step 2), a molar volume ratio of the phenolic hydroxyl precursor, the second compound, the solvent, and the nitro compounds is 0.06-0.12 mol:0.1-0.2 mmol:15-25 mL:0.1-0.2 mmol.

7. The preparation method according to claim 4, wherein in step 2), a reaction temperature is 0-30° C., and a reaction time is 20-26 h.

8. An application of a luminescent probe in a detection of human serum albumin and bovine serum albumin, wherein the luminescent probe has a structural formula shown in formula (I)

(I)

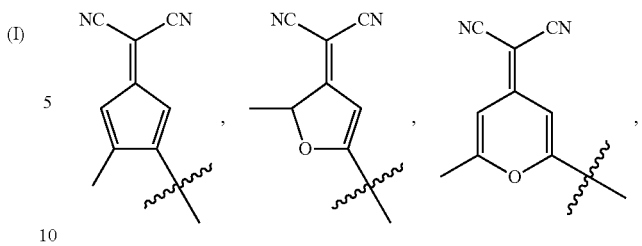

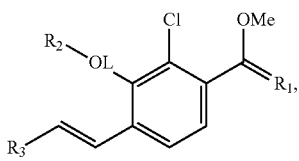

wherein $R_1$ is selected from one of

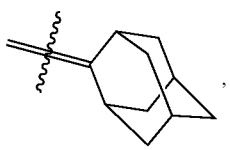,

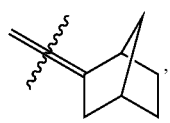,

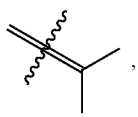,

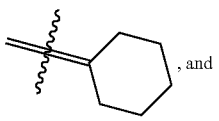, and

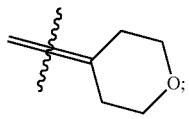;

$R_2$ is selected from one of

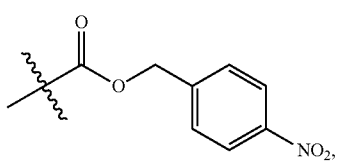,

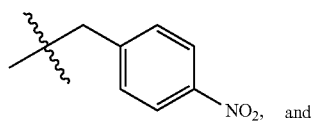, and

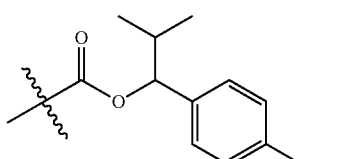

and $R_3$ is selected from one of wherein the application comprising the following steps: mixing a luminescent probe stock solution with a mixed solvent and a serum albumin stock solution in turn, afterwards, performing an incubation and detection in turn.

9. The application according to claim 8, wherein a concentration of the luminescent probe stock solution is $0.8 \times 10^{31\ 3} - 1.5 \times 10^{-3}$ M; the mixed solvent is prepared from dimethyl sulfoxide and a phosphate buffered saline (PBS) buffer solution, wherein a volume ratio of the dimethyl sulfoxide and the PBS buffer solution is 1:2-3, a pH value of the PBS buffer solution is 7.0-7.5; and a concentration of the serum albumin stock solution is $2.0 \times 10^{-4} - 1.0 \times 10^{-2}$ M.

10. The application according to claim 8, wherein a volume ratio of the luminescent probe stock solution, the mixed solvent, and the serum albumin stock solution is 20 μL:1.84-2 mL:0-160 μL; and an incubation temperature is 36.5-37.5° C., an incubation time is 42-46 min.

11. The preparation method according to claim 4, wherein in step 1), a reaction temperature is 20-30° C., and a reaction time is 5-7 h.

12. The preparation method according to claim 6, wherein in step 2), a reaction temperature is 0-30° C., and a reaction time is 20-26 h.

13. The application according to claim 8, wherein in the luminescent probe, the structural formula of the luminescent probe is

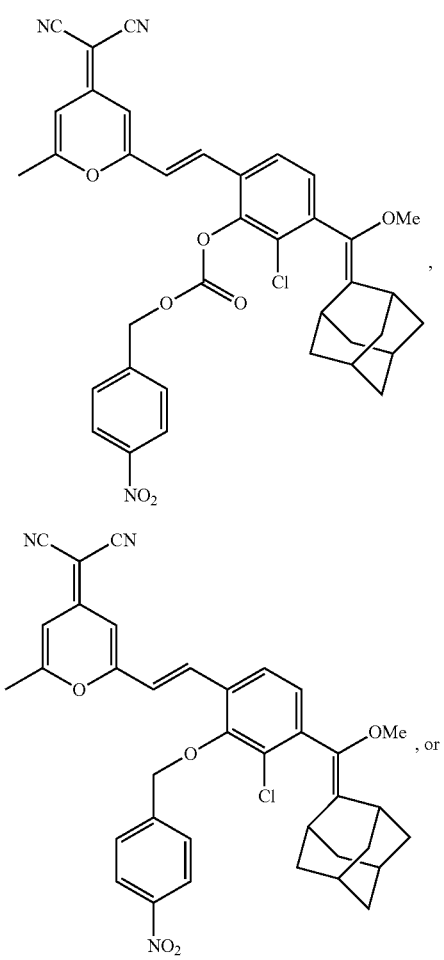
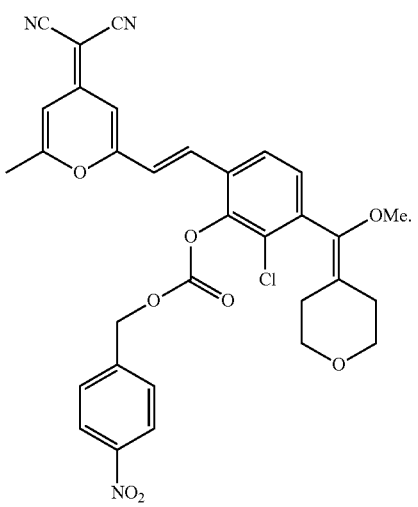
14. The application according to claim 9, wherein a volume ratio of the luminescent probe stock solution, the mixed solvent, and the serum albumin stock solution is 20 μL:1.84-2 mL:0-160 μL; and an incubation temperature is 36.5-37.5° C., an incubation time is 42-46 min.
* * * * *